United States Patent [19]

Tanaka et al.

[11] Patent Number: 5,130,058
[45] Date of Patent: * Jul. 14, 1992

[54] PHOTOCHROMIC COMPOUND, PROCESS FOR PRODUCTION THEREOF, USE THEREOF AND COMPOSITION CONTAINING SAID PHOTOCHROMIC COMPOUND

[75] Inventors: Takashi Tanaka, Shinnanyo; Kenji Tanaka; Satoshi Imura, both of Tokuyama; Yasuji Kida, Kudamatsu, all of Japan

[73] Assignee: Tokuyama Soda Kabushiki Kaisha, Yamaguchi, Japan

[*] Notice: The portion of the term of this patent subsequent to Nov. 21, 2006 has been disclaimed.

[21] Appl. No.: 373,100

[22] Filed: Jun. 29, 1989

[30] Foreign Application Priority Data

Jul. 1, 1988 [JP] Japan .................. 63-162663

[51] Int. Cl.$^5$ ................... G02B 5/23; G03C 1/725; C07D 207/00; C07D 307/77
[52] U.S. Cl. .................... 252/586; 252/589; 548/407; 549/234; 549/236; 549/239; 549/41; 549/44; 549/45; 549/47; 549/48; 549/42; 430/336; 430/339
[58] Field of Search ............ 252/586, 589; 548/407; 549/234, 23, 26, 236, 239, 41, 42, 44, 60, 43, 45, 47, 48; 430/336, 339

[56] References Cited

U.S. PATENT DOCUMENTS

| | | | |
|---|---|---|---|
| 4,685,783 | 8/1987 | Heller et al. | 252/586 |
| 4,882,438 | 11/1989 | Tanaka et al. | 548/407 |

FOREIGN PATENT DOCUMENTS

| | | | |
|---|---|---|---|
| 0140540 | 5/1985 | European Pat. Off. | |
| 0316179 | 5/1989 | European Pat. Off. | |
| 351112 | 1/1990 | European Pat. Off. | 549/44 |
| 2146327 | 4/1985 | United Kingdom | 252/586 |

*Primary Examiner*—Robert L. Stoll
*Assistant Examiner*—Philip Tucker
*Attorney, Agent, or Firm*—Wenderoth, Lind & Ponack

[57] ABSTRACT

A photochromic compound represented by the following general formula [I]

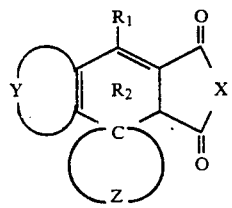

wherein

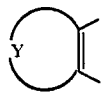

represents a divalent aromatic hydrocarbon group or a divalent heterocyclic group each of which may have a substituent,
$R_1$ represents a monovalent hydrocarbon group or a monovalent heterocyclic group each of which may have a substituent,

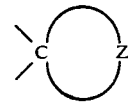

represents a norbornylidene or adamantylidene group which may have a substituent,
X represents an oxygen atom or a group of the formula $>N-R_3$ in which $R_3$ represents a hydrogen atom or a hydrocarbon group which may have a substituent, and
$R_2$ represents a monovalent hydrocarbon group which may have a substituent.

Also provided are a process for production of the photochromic compound, a composition containing the photochromic compound, and the use of the photochromic compound. The colored form of this photochromic compound has excellent thermal stability.

14 Claims, 3 Drawing Sheets

PHOTOCHROMIC COMPOUND, PROCESS FOR PRODUCTION THEREOF, USE THEREOF AND COMPOSITION CONTAINING SAID PHOTOCHROMIC COMPOUND

This invention relates to a novel compound having a photochromic action, processes for producing it, a composition comprising it, and its use. More specifically, it relates to a novel compound which changes reversibly in color from a colorless form to a colored form by the action of light containing ultraviolet rays such as sunlight or the light from a mercury lamp and has excellent thermal stability in colored form, processes for its production, a composition comprising it, and to Photochromism, which has aroused a particular interest for the last several years, denotes a phenomenon in which when light containing ultraviolet rays such as sunlight or the light from a mercury lamp is irradiated onto a certain compound, its color rapidly changes, and when the light irradiation is stopped and the compound is placed in a dark place, its color reversibly returns to the original color. Compounds having this property are called photochromic compounds. Photochromic compounds of various structures have been synthesized and proposed, but no particular common structure has been observed in these compounds.

Compounds represented by the following general formula

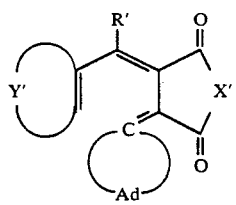

wherein

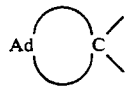

represents a substituted or unsubstituted adamantylidene group, R' represents a hydrogen atom, an alkyl group, an aryl group, an aralkyl group or a heterocyclic group, X' represents oxygen or the group >N—R" in which R" represents a hydrogen atom, an aryl group, an alkyl group or an aralkyl group, and

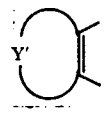

represents an aromatic group or an unsaturated heterocyclic group, are known as a series of photochromic compounds which absorb ultraviolet rays and are colored and rapidly return to their original color under white light (U.S. Pat. No. 4,220,708). These compounds are not at all colored, or hardly colored, under sunlight because they show a tendency to returning to a colorless form under white light. Furthermore, these compounds have the property of being thermally stable and not returning to the colorless form at room temperature and their use as a photomemory material by utilizing this property has recently been actively exploited. However, because the repetition life of their photochromism is short, they have not yet come into commercial acceptance.

Compounds of the above formula are known to be converted by heating into photochromic compounds of the following general formula which are colored under sunlight (see U.K. Patent Application No. 2,146,327)

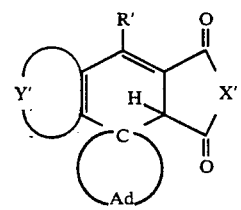

wherein

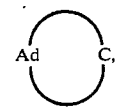

R', X' and

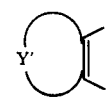

are the same as defined with regard to the above compounds.

It is believed that since the above photochromic compounds have rigid non-flexible cage-like adamantylidene groups, the single bond forming part of the six-membered ring is weakened and an electron cyclic ring-opening by irradiation of solar light is facilitated and consequently, the compounds become colored. However, the colored form of the above compound is thermally unstable and at room temperature and it completely returns to the colorless form in several seconds to several minutes. Hence, there is little possibility that these compounds will be used as photomemory material.

It has been desired therefore to develop photochromic compounds which reversibly repeat color formation and extinction over an extended duration, and have excellent thermal stability in the colored form, and which can be used as photomemory materials.

It is an object of this invention to provide a novel photochromic compound.

Another object of this invention is to provide a compound which reversibly changes from a colorless form to a colored form by the action of ultraviolet rays.

Still another object of this invention is to provide a photochromic compound having durability which can be used for a long period of time.

Yet another object of this invention is to provide a photochromic compound having practical utility.

A further object of this invention is to provide industrially advantageous processes for producing the photochromic compound.

A still further object of this invention is to provide a polymeric composition comprising the photochromic compound, and a photomemory material composed of the composition.

Other objects of the invention will become apparent from the following description.

These objects and advantages of this invention are achieved by a novel compound represented by general formula [I]

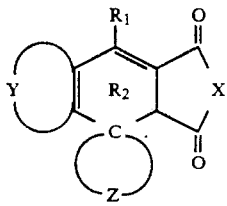

wherein

represents a divalent aromatic hydrocarbon group or a divalent heterocyclic group each of which may have a substituent, $R_1$ represents a monovalent hydrocarbon group or a monovalent heterocyclic group each of which may have a substituent,

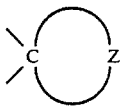

represents a norbornylidene or adamantylidene group which may have a substituent, X represents an oxygen atom or a group of the formula $>N-R_3$ in which $R_3$ represents a hydrogen atom or a hydrocarbon group which may have a substituent, and $R_2$ represents a monovalent hydrocarbon group which may have a substituent.

The compound of general formula [I] provided by this invention will be described in detail.

In general formula [I],

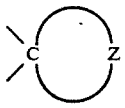

is a norbornylidene or adamantylidene group which may have a substituent. The norbornylidene group is represented by the following formula.

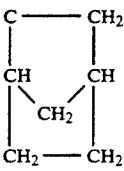

The adamantylidene group is represented by the following formula.

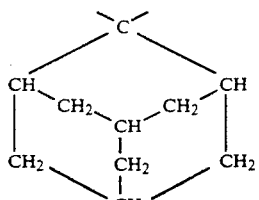

The above formulae show the skeletal structures of the norbornylidene group and the adamantylidene group having no substituent. One or more hydrogen atoms in the above formulae may be substituted by a substituent. The types and number of such substituents and the substitution positions may be selected according to the purpose and utility. When the norbornylidene or adamantylidene group has a plurality of substituents, they may be of the same or different kinds.

The suitable number of substituents, if present, is generally 1 to 5, preferably 1 to 3.

Examples of the substituents for the norbornylidene or adamantylidene group include a hydroxyl group, a nitro group, a cyano group, a carboxyl group, halogen atoms (e.g., fluorine, chlorine and bromine), alkylamino groups having 1 to 4 carbon atoms (e.g., methylamino or ethylamino), di($C_1$-$C_4$)alkylamino groups (e.g., dimethylamino or diethylamino), $C_1$-$C_4$ alkyl groups (e.g., methyl, ethyl, propyl and t-butyl), $C_1$-$C_4$ alkoxy groups (e.g., methoxy, ethoxy, propoxy and t-butoxy), $C_1$-$C_2$ haloalkyl groups (e.g., chloromethyl, trichloromethyl or trifluoromethyl), $C_2$-$C_{10}$ alkoxycarbonyl groups (e.g., methoxycarbonyl, ethoxycarbonyl and butoxycaronyl), ($C_1$-$C_4$)alkylcarbonyl($C_1$-$C_4$)alkyl groups (e.g., methylcarbonylmethyl and methylcarbonylethyl), $C_7$-$C_9$ aralkyl groups (e.g., benzyl, phenylethyl and phenylpropyl), $C_7$-$C_{15}$ aralkoxy groups (e.g., benzyloxy and phenylethoxy), $C_6$-$C_{10}$ aryl groups (e.g., phenyl, tolyl naphthyl), and $C_6$-$C_{10}$ aryloxy groups (e.g., phenoxy and 1-naphthoxy).

Of these substituents, the halogen atoms, the $C_1$-$C_4$ alkyl groups, the $C_1$-$C_4$ alkoxy groups, the $C_1$-$C_4$ alkylamino groups, the di($C_1$-$C_4$)alkylamino groups and the ($C_1$-$C_4$)alkylcarbonyl($C_1$-$C_4$)alkyl groups are preferred.

As

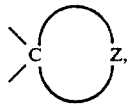

the adamantylidene group which have a substituent is preferable to the norbornylidene group which may have a substituent because of higher thermal stability. When

is an adamantylidene group which may have a substituent and X is an oxygen atom, a thermally stable colored form of photochromic compound can be obtained. Accordingly this combination is especially preferred.

When X is the group >N—$R_3$, $R_3$ is a hydrogen atom or a hydrocarbon group which may have a substituent. The hydrocarbon group is preferably a $C_1$–$C_4$ alkyl group, a $C_5$–$C_7$ cycloalkyl group, a $C_7$–$C_{10}$ aralkyl group or a $C_6$–$C_{10}$ aryl group. Specific examples include alkyl groups having 1 to 6 carbon atoms such as methyl, ethyl, propyl, n-butyl, iso-butyl and n-hexyl groups; cycloalkyl groups having 5 to 7 carbon atoms such as cyclopentyl and cyloheptyl groups; aralkyl groups having 7 to 10 carbon atoms such as benzyl, phenylethyl and phenylpropyl groups; and aryl groups having 6 to 10 carbon atoms such as phenyl, naphthyl, tolyl and xylyl groups.

These hydrocarbon groups may each be substituted by at least one atom or group selected from the class consisting of halogen atoms, a cyano group, a nitro group, a hydroxyl group, $C_1$–$C_6$ alkoxy groups, $C_6$–$C_{10}$ aryloxy groups,

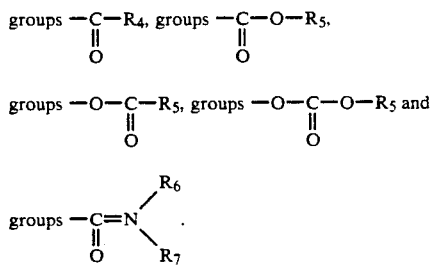

In these formulae, $R_4$ represents a $C_1$–$C_4$ alkyl group or a $C_6$–$C_{10}$ aryl group which may each be substituted by a halogen atom. $R_5$ is a $C_1$–$C_4$ alkyl may be substituted by a halogen atom or a nitro group, or a $C_6$–$C_{10}$ aryl group which may be substituted by a cyano group, or a $C_7$–$C_{10}$ aralkyl group. $R_6$ and $R_7$ are identical or different, and each represents a hydrogen atom, a $C_1$–$C_4$ alkyl group, a $C_7$–$C_{10}$ aralkyl group or a $C_6$–$C_{10}$ aryl group. In the above substituents, examples of the halogen atoms are fluorine, chlorine, bromine and iodine atoms. Examples of the $C_1$–$C_6$ alkoxy groups include methoxy, ethoxy, propoxy and butoxy groups. The $C_6$–$C_{10}$ aryloxy groups are, for example, phenoxy, naphthoxy and tolyloxy groups. The $C_6$–$C_{10}$ aryl groups are, for example, phenyl, naphthyl and tolyl groups. Examples of the $C_7$–$C_{10}$ aralkyl groups are benzyl, phenylethyl and phenylpropyl groups.

Usually 1 to 5, preferably 1 to 3, such substituent, may be substituted on the above hydrocarbon groups. When there are two or more substituents, they may be identical or different.

When X is the group >N—$R_3$, $R_3$ is preferably a $C_1$–$C_6$ alkyl group, a $C_5$–$C_7$ cycloalkyl group or a $C_7$–$C_{10}$ aralkyl group each of which may be substituted by a halogen atom, a cyano group, a nitro group, a $C_1$–$C_6$ alkoxy group or the

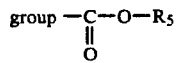

in which $R_5$ is a $C_1$–$C_4$ alkyl group which may be substituted by a halogen atom or a nitro group, or a $C_6$–$C_{10}$ aryl group which may be substituted by a cyano group.

In general formula [I], $R_1$ represents a monovalent hydrocarbon group or a monovalent heterocyclic group each of which may be substituted. The monovalent hydrocarbon group for $R_1$ may be an aliphatic, alicyclic or aromatic hydrocarbon group, preferably a $C_1$–$C_{20}$, especially $C_1$–$C_6$, alkyl group such as methyl, ethyl, propyl and butyl groups, a $C_6$–$C_{10}$ aryl group such as phenyl, tolyl, xylyl and naphthyl groups, or a $C_7$–$C_{10}$ aralkyl group such as benzyl, phenylethyl, phenylpropyl and phenylbutyl groups.

The monovalent heterocyclic group for $R_1$ is preferably a 5- or 6-membered monoheterocyclic group having 1 to 3, preferably 1 or 2, hetero atoms selected from nitrogen, oxygen and sulfur atoms, or a fused heterocyclic group resulting from fusion of a benzene ring thereto. Specific examples of the heterocyclic group include nitrogen-containing heterocyclic groups such as pyrrolyl, pyridyl, quinolyl and piperidyl groups, oxygen-containing heterocyclic groups such as furyl, benzofuryl and oxolanyl groups, and sulfur-containing heterocyclic groups such as benzothienyl and thiolanyl groups.

The hydrocarbon group or heterocyclic group for $R_1$ may have a substituent. The number of such substituents on $R_1$ is at most 5, preferably at most 3. Specific examples of the substituents may be the same as given above with regard to

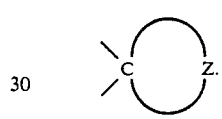

Examples of preferred $R_1$ groups include $C_1$–$C_6$ alkyl groups which may be substituted by a halogen atom pr a $C_1$–$C_4$ alkoxy group; $C_7$–$C_{10}$ aralkyl groups which may be substituted by halogen atoms; $C_6$–$C_{10}$ aryl groups which may be substituted by a halogen atom, a nitro group or a $C_1$–$C_4$ alkoxy group; 5- or 6- membered monoheterocyclic groups containing 1 to 3 hetero atoms; and fused heterocyclic groups resulting from fusion of a benzene ring to the above monoheterocyclic groups.

Especially preferred $R_1$ groups are $C_1$–$C_6$ alkyl groups, $C_7$–$C_{10}$ aralkyl groups, and $C_6$–$C_{10}$ aryl groups which may be substituted by a halogen atom, a nitro group or a $C_1$–$C_4$ alkoxy group.

$R_2$ in general formula [I] in this invention is a monovalent hydrocarbon group which may have a substituent. That $R_2$ is a monovalent hydrocarbon which may be substituted is of great technical significance to the thermal stability of the colored form of the compound of formula [I]. In this case, the colored form of the compound [I] has much improved thermal stability over the case in which $R_2$ is not a hydrocarbon ($R_2$ is a hydrogen atom). Accordingly, the compounds of this invention can be used as a photomemory material.

$R_2$ in general formula [I] is preferably a $C_1$–$C_6$ alkyl group, a $C_5$–$C_7$ cycloalkyl group, a ($C_5$–$C_7$) cycloalkyl($C_1$–$C_4$)alkyl group, a $C_7$–$C_{10}$ aralkyl group, or a $C_6$–$C_{10}$ aryl group. Each of these groups may be substituted by a halogen atom, a cyano group, a nitro group, a hydroxyl group, a $C_1$–$C_6$ alkoxy group, a $C_6$–$C_{10}$ aryloxy group which may be substituted by a halogen atom, a $C_7$–$C_{10}$ aralkoxy group, the

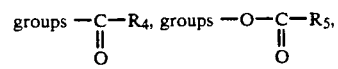

-continued

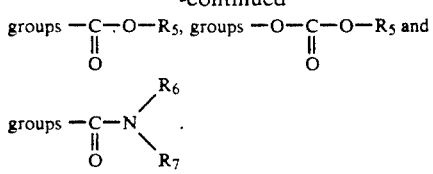

The number of such substituents may be 1 to 5, preferably 1 to 3. When there are two or more substituents, they may be of the same or different kind. In the above substituents, $R_4$, $R_5$, $R_6$ and $R_7$ are the same as defined above with regard to $>N-R_3$.

Specific preferred examples of $R_2$ and substituents on it include $C_1$-$C_6$ alkyl groups such as methyl, ethyl, propyl, n-butyl, iso-butyl, t-butyl, n-pentyl and iso-pentyl groups; $C_5$-$C_7$ cycloalkyl groups such as cyclopentyl, cyclohexyl and cycloheptyl groups, ($C_5$-$C_7$)cycloalkyl($C_1$-$C_4$)alkyl groups such as cyclohexylmethyl and cyclohexylethyl groups; $C_7$-$C_{10}$ aralkyl groups such as benzyl, phenylethyl and phenylpropyl groups; $C_6$-$C_{10}$ aryl groups such as phenyl, naphthyl, tolyl and xylyl groups; halogen atoms such as fluorine, chlorine and iodine atoms; $C_1$-$C_6$ alkoxy groups such as methoxy, ethoxy, propoxy and butoxy groups; $C_6$-$C_{10}$ aryloxy groups such as phenoxy, naphthoxy and tolyloxy groups; and $C_7$-$C_{10}$ aralkoxy groups such as benzyloxy and phenylethoxy groups.

The above monovalent hydrocarbon groups other than the $C_6$-$C_{10}$ aryl groups are preferred as $R_2$.

in general formula [I] represents a divalent aromatic hydrocarbon group or a divalent heterocyclic group each of which may have a substituent. The aromatic hydrocarbon group preferably has 6 to 14 carbon atoms, specifically a phenylene, napthalene or phenanthrene group. The heterocyclic group is preferably a 5- or 6-membered monoheterocyclic group having 1 to 3, preferably 1 or 2 hetero atoms selected from nitrogen, oxygen and sulfur atoms. Specific examples of the heterocyclic group are furanyl, pyrrolyl, thiophenyl, benzofuranyl, indolyl and benzothiophenyl groups.

The aromatic hydrocarbon group or heterocyclic group may each have at least one substituent selected from halogen atoms, nitro groups, cyano groups, $C_1$-$C_4$ alkyl groups, $C_1$-$C_4$ alkylamino groups, di($C_1$-$C_4$)alkylamino groups, phenyl groups and $C_1$-$C_4$ alkoxyphenyl groups. The number of these substituents may be 1 to 5, preferably 1 to 3. When there are two or more substituents, they may be identical or different. When two alkyl groups are substituted, they may be bonded to each other to form a ring.

In the substituents on the aromatic hydrocarbon group or the heterocyclic group in

examples of the halogen atom are fluorine, chlorine, bromine and iodine atoms. Examples of $C_1$-$C_4$ alkoxy groups are methoxy, ethoxy, propoxy and butoxy groups. Examples of $C_1$-$C_4$ alkylamino groups are methylamino, ethylamino and butylamino groups. Examples of the di($C_1$-$C_4$)alkylamino groups are dimethylamino, diethylamino, methylethylamino, dipropylamino and dibutylamino groups.

Preferred examples of

include a divalent benzene ring, a divalent naphthalene ring, a divalent furan ring, a divalent pyrrole ring, a divalent thiophene ring, a divalent benzofuran ring, a divalent indole ring, a divalent benzothiophene ring and a divalent tetrahydrobenzothiophene ring. These rings may be substituted by an atom or group selected from the class consisting of halogen atoms, nitro groups, cyano groups, $C_1$-$C_4$ alkyl groups, $C_1$-$C_4$ alkoxy groups, $C_1$-$C_4$ alkylamino groups, di($C_1$-$C_4$)alkylamino groups, phenyl groups and $C_1$-$C_4$ alkoxyphenyl groups.

Most preferred compounds of this invention are those of general formula [I] in which X is an oxygen atom or the group $>N-R_3$ wherein $R_3$ represents a $C_1$-$C_6$ alkyl group which may be substituted by a halogen atom, a cyano group, or a $C_2$-$C_5$ alkoxycarbonyl group,

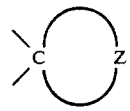

represents a norbornylidene or adamantylidene group, $R_1$ represents a alkyl group or a $C_6$-$C_{10}$ aryl group, $R_2$ is a $C_1$-$C_4$ alkyl group which may be substituted by a $C_2$-$C_5$ alkoxycarbonyl group, and

is a divalent furan ring, a divalent pyrrole ring or a divalent thiophene ring.

The compound of general formula [I] may be produced by any manufacturing process, and is not limited by the type of the manufacturing process. Preferred typical processes are described below without any intention of limiting the invention thereby.

Typically, the compound of general formula [I] can be obtained by reacting a compound represented by the following general formula [II]

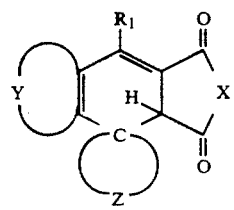

[II]

wherein

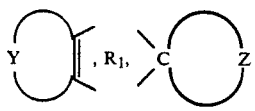

and X are as defined in general formula [I], with a halogen compound represented by the following general formula [III]

Hal—R$_2$     [III]

wherein Hal represents a chlorine, bromine or iodine atom, and R$_2$ is as defined in general formula [I], in the presence of an alkali metal or an alkali metal carbonate or after the compound of general formula [I] is reacted with the alkali metal or its carbonate.

The alkali metal used in this process may be, for example, sodium, potassium or lithium. Examples of the alkali metal carbonate are sodium carbonate, potassium carbonate and lithium carbonate. The proportion of the alkali metal or its carbonate is 10 to 20 moles per mole of the compound of general formula [II]. The proportion of the halogen compound of general formula [III] is 0.5 to 20 moles per mole of the compound of formula [II].

Preferably, this reaction is carried out by using a solvent. Examples of the solvent that can be preferably used include polar aprotic solvents such as dimethylformamide, N-methylpyrrolidone, dimethyl sulfoxide, hexamethylphosphoric triamide, tetrahydrofuran and 1,4-dioxane.

The reaction is carried out at a temperature of usually 0° to 200° C., preferably 0° to 50° C. for a period of 1 to 170 hours, preferably 5 to 50 hours under a pressure from normal atmospheric pressure to 5 atmospheres, preferably atmospheric pressure to 3 atmospheres. After the reaction, the solvent is removed, and the product is dissolved in a solvent such as diethyl ether. The insoluble alkali metal halide, etc. are removed by filtration. The residue is purified by silica gel chromatography using a solvent such as chloroform or dichloromethane as an eluent to give the desired product.

In the above process, there can be employed a procedure in which the compound of general formula [II] is first reacted with the alkali metal or its carbonate, and then with the halogen compound of general formula [III]. This is not limitative, however. For example, when the compound of general formula [II], the alkali metal or its carbonate, and the halogen compound of general formula [III] are simultaneously contacted, the above consecutive reactions proceeded and the compound of general formula [I] of the invention can be obtained.

The compound of general formula [I] generally exists as a pale yellow solid at room temperature, and can generally be identified by the following procedures (a) to (c).

(a) The types and number of protons existing in the molecule can be determined by measuring the proton nuclear magnetic resonance spectrum (H$^1$-NMR) of the compound. Specifically, in the H$^1$-NMR spectrum, there appear a peak based on aromatic protons near $\delta$7-8 ppm, a broad peak based on protons derived from the adamantylidene or norbornylidene group near $\delta$1.2-2.5 ppm, and a peak based on the alkyl group in R$^1$ near $\delta$1.2-4.0 ppm (where R$_1$ is an alkyl group). By comparing the intensities of these peaks, the number of protons of the bonding groups can be determined.

(b) By elemental analysis, the weight percentages of carbon, hydrogen, nitrogen, sulfur and halogen can be determined. The weight percent of oxygen can be calculated by subtracting the total weight percentage of the elements from 100. Accordingly, the composition of the product can be determined.

(c) The types of carbons present in the molecule can be determined by measuring the $^{13}$C-nuclear magnetic resonance spectrum of the compound. There appear a peak derived from carbons of the adamantylidene or norbornylidene group near $\delta$27-52 ppm, a peak based on carbons of the alkyl group in R$_1$ near $\delta$15-35 ppm (where R$_1$ is an alkyl group), a peak based on the carbons of the aromatic hydrocarbon group or the unsaturated heterocyclic group near $\delta$110 to 150 ppm, and a peak based on the carbon of >C=O near $\delta$160-170 ppm.

The compound of general formula [II] that can be used as a starting material in the above process can be produced, for example, by the following process.

A compound of general formula [II] in which X is an oxygen atom may be produced by cyclizing a compound of the following formula [IV]

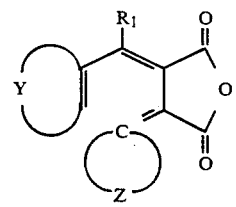     [IV]

wherein

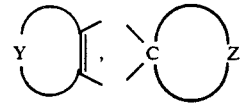

and R$_1$ are as defined in general formula [I]. The cyclization is carried out, for example, by heating the compound to a temperature of 160° to 220° C., or carrying out this heating by ultraviolet irradiation, or by bringing the compound into contact with a Lewis acid catalyst. The Lewis acid catalyst may be a known compound such as SnCl$_4$, TiCl$_4$, SbCl$_5$ and AlCl$_3$. The amount of the Lewis acid used is not particularly restricted, but usually amounts of 0.001 to 1 mole per mole of the compound to be cyclized are preferred.

A compound of general formula [II] in which X is the group >N—R$_3$ may be produced by reacting the compound of general formula [IV] with an amine compound of the following general formula [V]

H$_2$N—R$_3$     [V]

wherein R$_3$ is as defined in general formula [I], to obtain an imide compound of the general formula [IV-a]

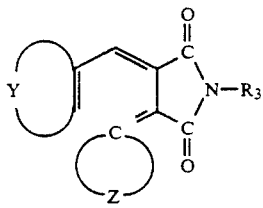

[IV-a]

wherein all symbols are as defined, and then cyclizing the imide compound under the same conditions as described above.

Furthermore, a compound of general formula [II] in which X is the group >N—$R_3$ can be obtained by reacting an imide compound represented by general formula [III]

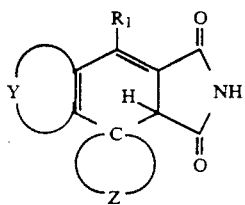

[VI]

wherein

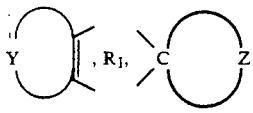

and X are as defined in general formula [I], with an alkali metal, and then reacting the product with a bromine compound of general formula [VII]

Br—$R_3$      [VII]

wherein $R_3$ is as defined in general formula [I].

The compound of general formula [I] provided by this invention is well soluble in general organic solvents such as toluene, chloroform and tetrahydrofuran. When the compound [I] is dissolved in such a solvent, the solution has a reversible photochromic action such that it is almost colorless and transparent, and when sunlight or ultraviolet rays are irradiated onto it, it develops a color. Even when the light is shut off, its coloration hardly changes at ordinary temperature. When it is heated to about 80° C., the state of coloration is stable and it does not return to its original colorless form. However, when white light is irradiated, it rapidly attains the original colorless form. The compound of formula [I] also exhibits this photochromic action in a polymeric solid matrix with a reversing speed on the order of seconds. A polymer for forming such a polymeric material may be any polymer in which the compound [I] can be dispersed uniformly. The molecular weight of the polymer is selected from 500 to 500,000. Examples of optically desirable polymers include polymethyl acrylate, polyethyl acrylate, polymethyl methacrylate, polyethyl methacrylate, polystyrene, polyacrylonitrile, polyvinyl alcohol, polyacrylamide, poly(2-hyroxyethyl methacrylate), polydimethylsiloxane, polycarbonate and poly(allyl diglycol carbonate); and copolymers obtained by copolymerizing the monomers constituting the above polymers either with each other or with other monomers.

The amount of the compound [I] to be dispersed in the above polymer is generally 0.001 to 70 parts by weight, preferably 0.005 to 30 parts by weight, especially preferably 0.1 to 15 parts by weight, per 100 parts by weight of the polymer.

The compounds represented by general formula [I] generally exist as colorless to pale yellow crystalline solids at room temperature and atmospheric pressure. The crystalline solids themselves have photochromism. When a crystalline solid of the compound of general formula [I] is irradiated with light containing ultraviolet rays, its coloration does not change at all at room temperature even if the light is shut off. Furthermore, when it is heated to about 80° C., the state of coloration is stable and it does not return to the original colorless form. But when white light is irradiated, it rapidly returns to its original colorless form reversibly, thus showing photochromism. Furthermore, the colored form of the photochromic compounds of this invention is thermally stable as compared with conventional fulgide compounds, and hardly returns to its original colorless form at about 80° C. When white light is irradiated, the colored form rapidly returns to its original colorless form reversibly. This repeated changes have excellent durability.

Accordingly, the compounds of this invention can be broadly utilized as a photochromic material. For example, they can be utilized in various recording materials superseding silver salt photographic materials, for example in memory materials, printing photographic materials, recording materials for a cathode ray tube, photographic materials for laser and photographic materials for holography. The photochromic material containing the compound of this invention can also be utilized as a photochromic lens material, an optical filter material, a display material, an actinometer, or a decorative material.

The photochromic compounds represented by general formula [I] show photochromism in solution or in a polymeric solid matrix, or their crystals themselves show photochromism. These compounds in a general condition are stably colorless or pale yellow, and immediately develop a color upon irradiation of ultraviolet rays. Even when the ultraviolet irradiation is stopped, their colored state is thermally stable even at 80° C., and when white light is irradiated, it rapidly returns to its colorless form. They also have the property of repeating these color changes.

In general formula [I], $R_2$ is the above-specified substituents and not a hydrogen atom. Compounds of general formula [I] in which $R_2$ is the specified substituents have good thermal stability in the colored state, and return to their original colorless form only when white light is irradiated. They repeat these color changes with good durability. This is clear from the fact that in the following Examples and Comparative Examples, the photochromic properties of the compounds of this invention in which $R_2$ represents hydrocarbon groups which may have various substituents had better photochromic properties (thermal stability and durability of color density) than compounds of formula [I] in which $R_2$ is a hydrogen atom.

The following examples illustrate the present invention in greater detail without limiting the invention thereby.

EXAMPLE 1

A compound of the following formula (3.4 g; 0.01 mole)

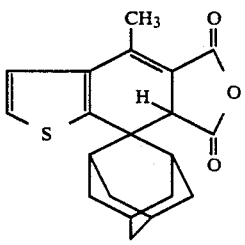

was dissolved in 100 cc of N,N-dimethylformamide, and 13.8 g (0.1 mole) of potassium carbonate and 14.1 g (0.1 mole) of methyl iodide were added. They were reacted at room temperature for 72 hours to give a fulgide compound (1) of the following formula. This compound was purified by chromatography on silica gel using chloroform and hexane as an eluent, and obtained in a yield of 17% as pale yellow crystals from ether. The elemental analysis values of this compound were C 70.92%, H 6.32%, O 12.79% and S 9.97% which very well agreed with C 71.16%, H 6.26%, O 13.54%, S 9.04% calculated for $C_{21}H_{22}O_3S$. Its proton nuclear magnetic resonance spectrum showed a peak of 2H based on the protons of the thiophene ring near $\delta 7.0-7.5$ ppm, a peak of 3H based on the protons of —$CH_3$ bond near $\delta 2.7$ ppm, a peak of 3H based on the protons of the methyl group of the reacted methyl iodide near $\delta 1.3$ ppm, and a peak of 14H based on the protons of the adamantylidene group near $\delta 1.3-2.5$ ppm.

Figure 1:
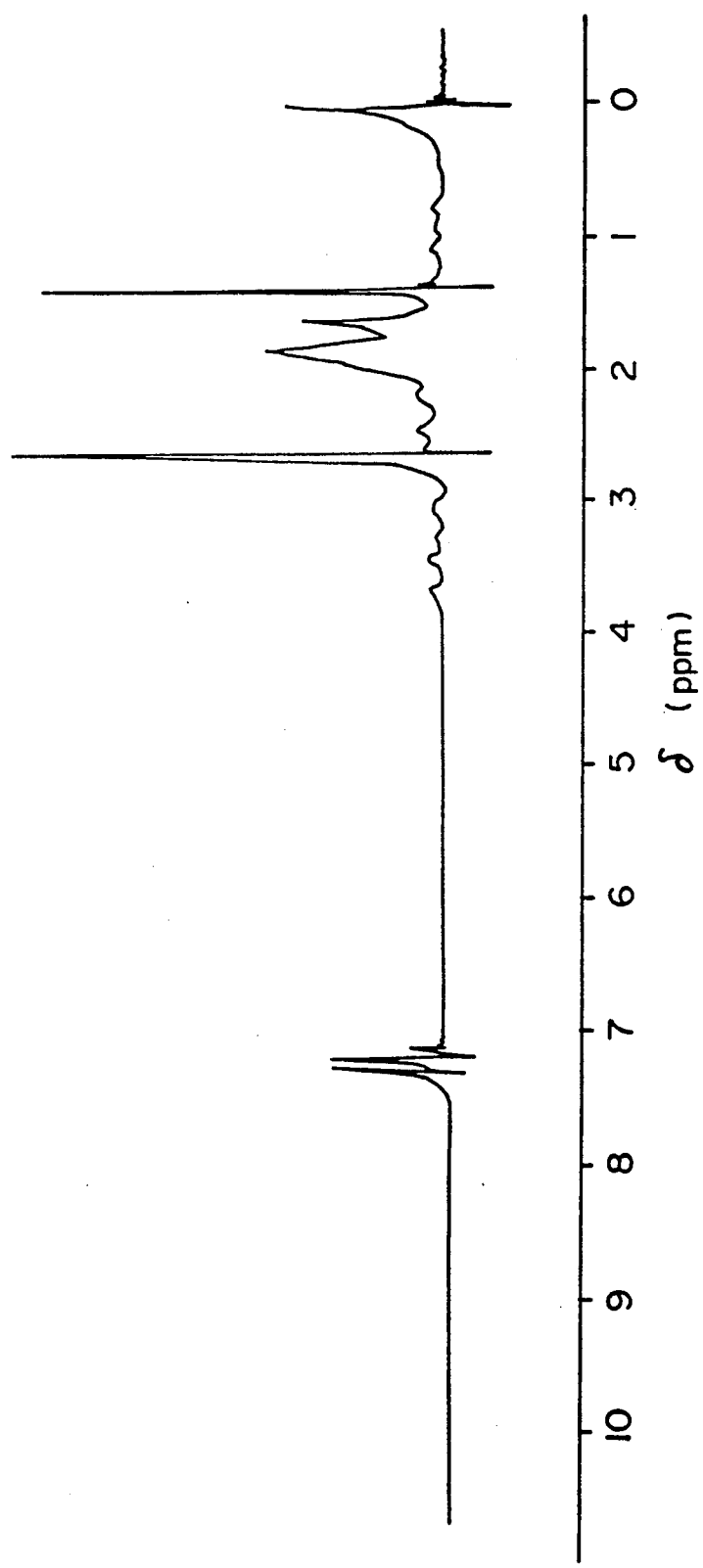
FIG. 1 is the proton nuclear magnetic resonance spectrum of the product obtained in Example 1.

The $^{13}C$-nuclear magnetic resonance spectrum of this compound showed a peak based on the carbons of the adamantylidene group near $\delta 27-50$ ppm, a peak based on the carbon of the methyl group near $\delta 15-20$ ppm, a peak based on the carbon atoms of the thiophene ring near $\delta 110-160$ ppm and a peak based on the carbon of the >C=O near $\delta 160-170$ ppm (see FIG. 1).

The above results led to the determination that the isolated product is a photochromic compound (1) of the following structural formula.

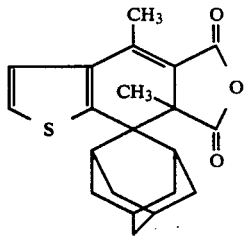

(1)

EXAMPLE 2

A fulgide compound of the following formula (3.0 g; 0.01 mole)

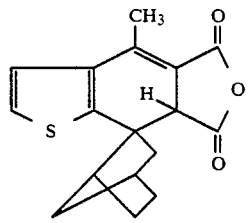

was dissolved in tetrahydrofuran, and reacted with 1 9 of potassium at room temperature to give 2.5 g of the following compound.

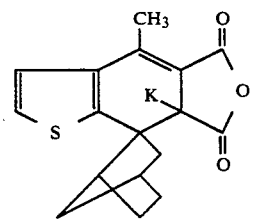

Figure 2:
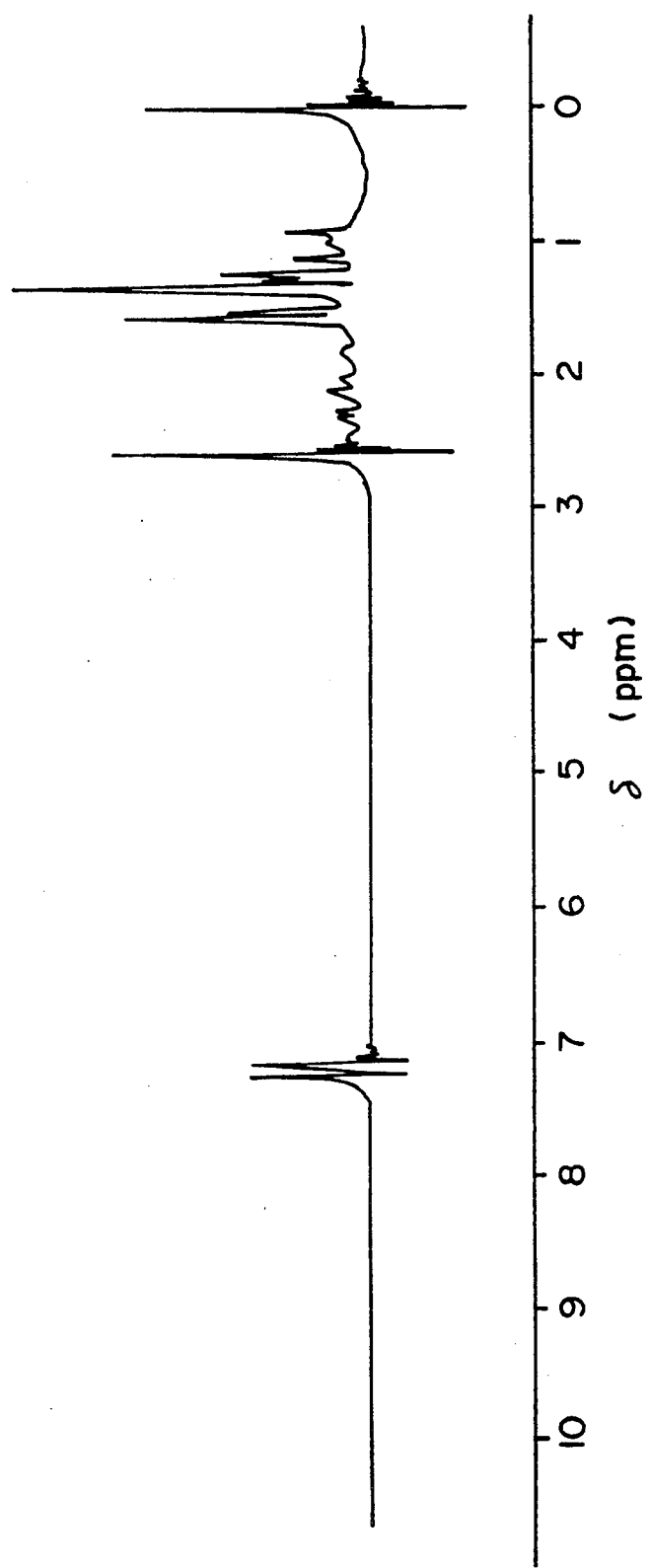
FIG. 2 is the proton nuclear magnetic resonance spectrum of the product obtained in Example 2.

This compound was reacted with 7.1 g (0.05 mole) of methyl iodide in N-mehylpyrrolidone to form a photochromic compound (2) below. It was purified by chromatography on silica gel using dichloromethane as an eluent, and obtained in a yield of 21.2% as pale yellow crystals from ether. The elemental analysis values of this compound were C 68.63%, H 5.81%, 0 15.21%, S 10.36% which well agreed with C 68.79%, H 5.73%, O 15.27% and S 10.20% calculated for $C_{18}H_{18}O_3S$. Its proton nuclear magnetic resonance spectrum showed a peak of 2H based on the protons of the thiophene ring near $\delta 7.0-7.5$ ppm, a peak of 3H based on the proton of the —$CH_3$ bond near $\delta 2.66$ ppm, a peak of 3H based on the proton of the reacted methyl group near $\delta 1.3$ ppm, and a peak of 10H based on the protons of the norbornylidene group near $\delta 1.5-2.0$ ppm (see FIG. 2).

Its $^{13}C$-nuclear magnetic resonance spectrum showed a peak based on the carbons of the norbornylidene group near $\delta 20-45$ ppm, a peak based on the carbon of the methyl group near $\delta 15-20$ ppm, a peak based on the carbons of the thiophene ring near $\delta 110-160$ ppm and a peak based on the carbon of the >C=O bond near $\delta 160-170$ ppm.

The above results led to the determination that the isolated product is a photochromic compound (2) of the following formula.

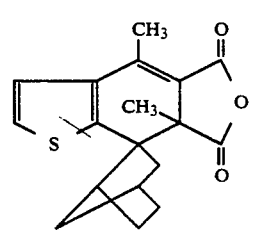

(2)

EXAMPLE 3

A fulgide compound of the following formula (3.39 g; 0.01 mole)

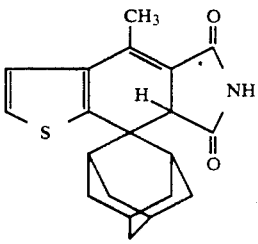

was dissolved in 100 cc of dimethyl sulfoxide and 212 g (0.2 mole) of sodium carbonate and 30.6 g (0.2 mole) of methyl bromoacetate were added. They were reacted at room temperature for 70 hours to give a fulgide compound (3) of the formula given below. This compound was purified by chromatography on silica gel using dichloromethane as an eluent and obtained in a yield of 15.3% as pale yellow crystals from ether and hexane. The elemental analysis values of this compound were C 64.52%, H 6.03%, N 2.88%, O 20.1% and S 6.47% which very well agreed with C 64.60%, H 6.00%, N 2.90%, O 19.86%, S 6.63% calculated for $C_{26}H_{29}NO_6S$. Its proton nuclear magnetic resonance spectrum showed a peak of 2H based on the protons of the thiophene ring near δ7.0–7.5 ppm, a peak of 3H based on the protons of —CH$_3$ near δ2.60 ppm, two peaks of 6H based on the methyl group bonded to

bond near δ3.4–3.8, a peak of 2H based on the methylene group in the

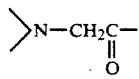

bond near δ4.4, a peak of 2H based on the methylene group of the

Figure 3:
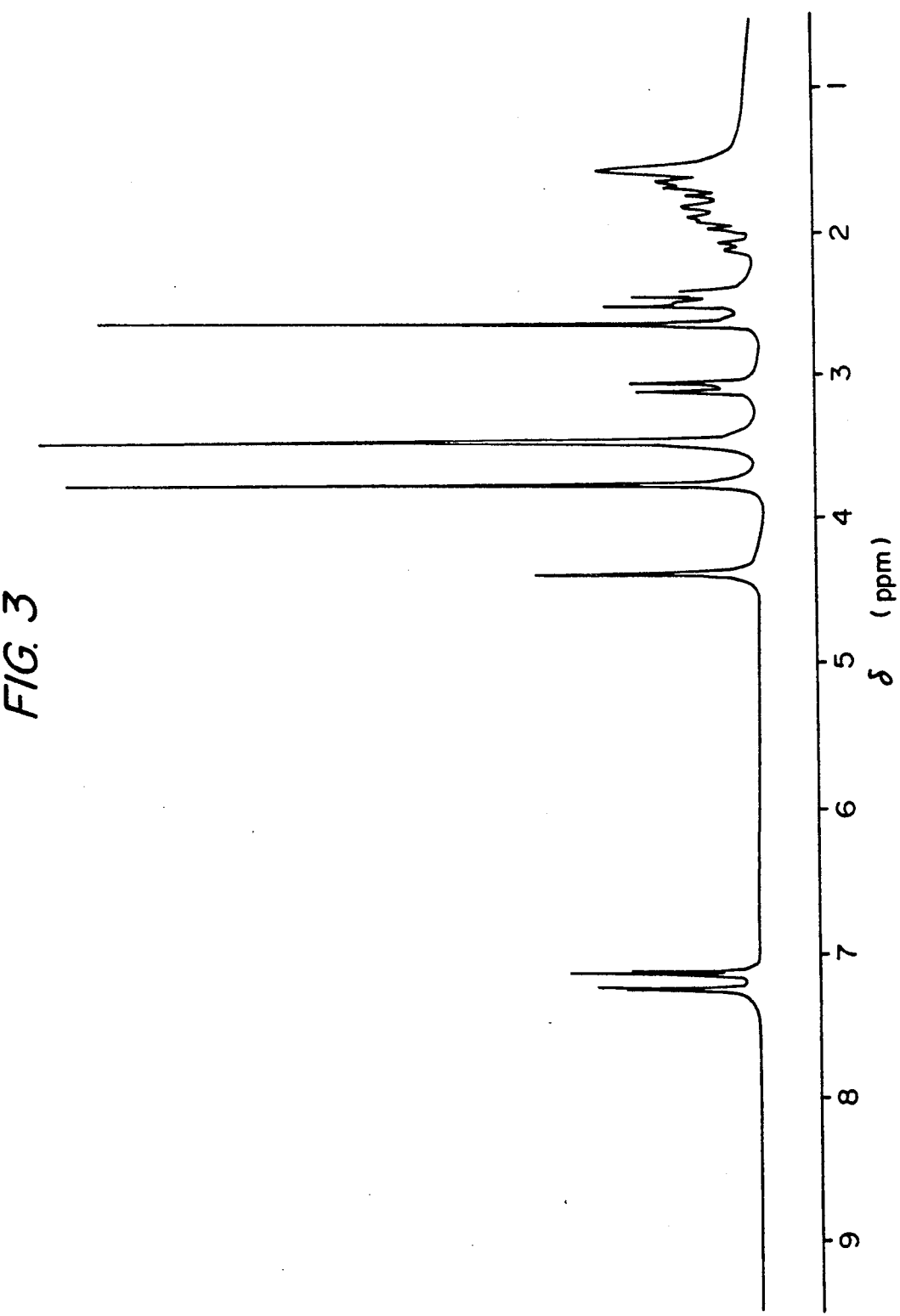
FIG. 3 is the proton nuclear magnetic resonance spectrum of the product obtained in Example 5.

bond near δ3.0 ppm and a peak of 14H based on the protons of the adamantylidene group near δ1.5–2.0 ppm (see FIG. 3).

When its $^{13}$C-nuclear magnetic resonance spectrum was measured, a peak based on the carbon atoms of the adamantylidene group appeared near δ27–50 ppm; a peak based on the carbon of the methyl group of the

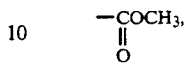

near δ50–60 ppm; a peak based on the carbons of the thiophene ring, near δ110–160 ppm; a peak based on the carbon of the >C=O bond, near 160–180 ppm; a peak based on the carbon of —CH$_3$, near δ15 ppm; and a peak based on the carbon of the methylene group of the

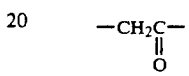

bond, near δ50–60 ppm.

The above results led to the determination that the isolated product is a photochromic compound (3) of the following structural formula

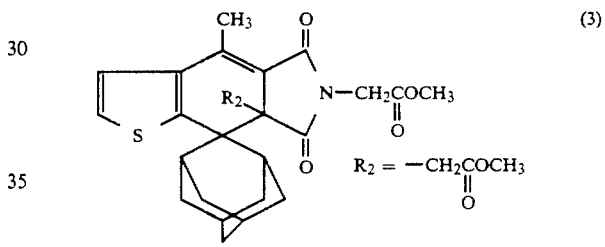

EXAMPLES 4–50

In the same way as in Examples 1 to 3, photochromic compounds were synthesized from the materials shown in Table 1-A.

The elemental analysis values, proton nuclear magnetic resonance spectra, $^{13}$C-nuclear magnetic resonane spectra of the resulting compounds were measured, and they were identified as compounds having the structural formulae (4) to (59) shown in Table 1-A. The elementral analysis values of the resulting compounds are shown in Table 1-B.

TABLE 1-A

| No. | Starting material | product | Yield (%) |
|---|---|---|---|
| 4 | (structure with C2H5, H, S, phenyl groups and Cl—CH2-phenyl) | (structure with C2H5, R2, S, phenyl groups; R2 = —CH2-phenyl) | 19 |
| 5 | (structure with phenyl, H, F, S, Br groups and CH3-CH(Br)-CH3) | (structure with phenyl, R2, F, S, Br groups; R2 = —CH(CH3)2) | 20 |

TABLE 1-A-continued
| No. | Starting material | product | Yield (%) |
|---|---|---|---|
| 6 | 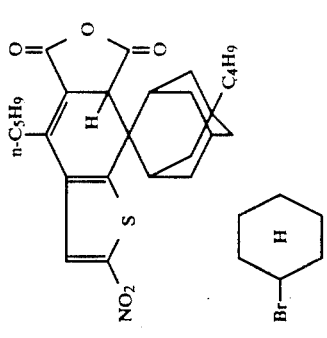 | 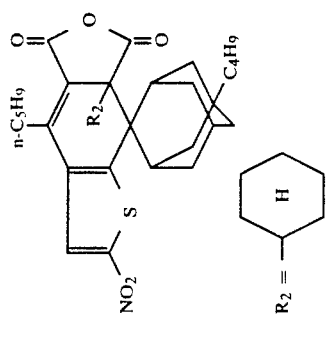 | 21 |
| 7 | 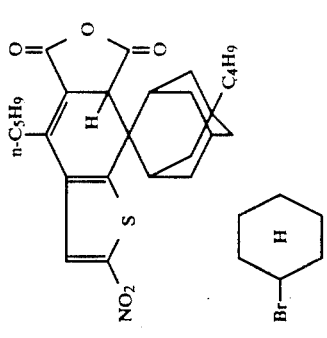 | 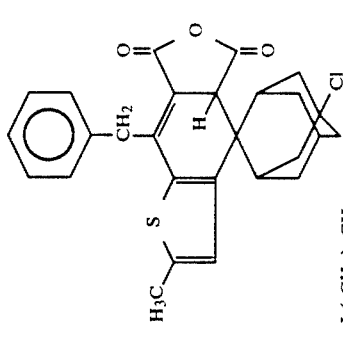 | 20 |

TABLE 1-A-continued

| No. | Starting material | product | Yield (%) |
|---|---|---|---|
| 8 | (structure with CH₃-phenyl, OCH₃, adamantane, BrCH₂CH₂-C₆H₄-CH₃) | (structure with R₂ substituent, R₂ = —CH₂CH₂-C₆H₄-CH₃) | 21 |
| 9 | (structure with phenyl-(CH₂)₃, Cl, adamantane, Br—CH₂C(CH₃)₂CH₃) | (structure with R₂ substituent, R₂ = —CH₂C(CH₃)₂CH₃) | 25 |

TABLE 1-A-continued

| No. | Starting material | product | Yield (%) |
|---|---|---|---|
| 10 | (structure with N-pyrrolyl, n-C₅H₉, SOCH₃, adamantane spiro, H); ICH₂CCH=O | (structure with R₂ group); R₂ = —CH₂CCH=O | 24 |
| 11 | (structure with phenyl-S, adamantane spiro, Cl, Cl, O, H); BrCH₂CF₃ | (structure with R₂ group); R₂ = —CH₂CF₃ | 23 |

TABLE 1-A-continued

| No. | Starting material | product | Yield (%) |
|---|---|---|---|
| 12 | (structure with OCH$_3$-phenyl, anhydride, adamantyl, N-phenyl vinyl, and 4-nitrobenzyl group; R shown as BrCH$_2$C(CH$_3$)H) | (same scaffold with R$_2$ = —CH$_2$C(CH$_3$)$_2$—, 4-nitrobenzyl) | 16 |
| 13 | (naphthyl-substituted anhydride scaffold with N-CH$_3$, Br-vinyl, cyclobutyl(CH$_3$)$_2$, C$_2$H$_5$CHBr—CCl(CH$_3$)) | (same scaffold; R$_2$ = —CH(C$_2$H$_5$Cl)—C(Cl)(CH$_3$)—) | 19 |

TABLE 1-A-continued
| No. | Starting material | product | Yield (%) |
|---|---|---|---|
| 14 | 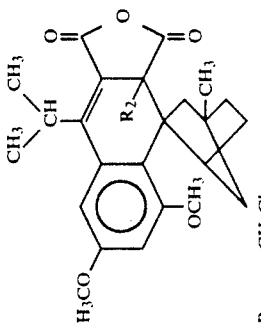 | 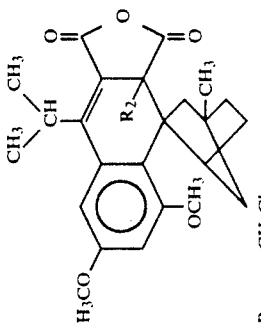 | 25 |
| 15 | 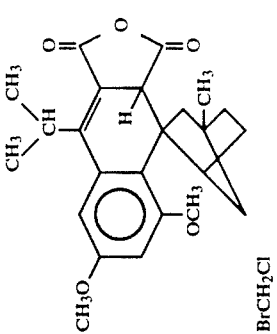 | 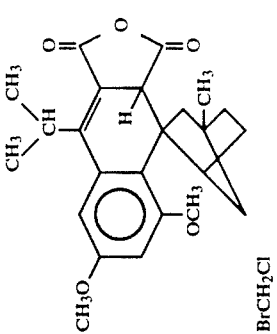 | 21 |
| 16 | 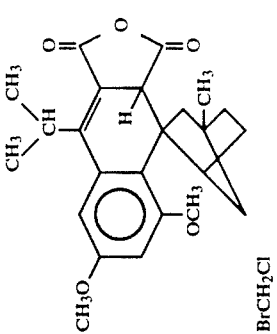 | 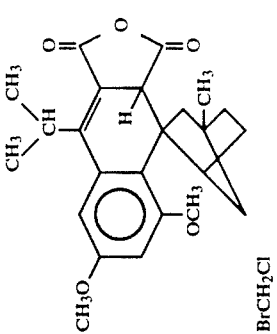 | 19 |

TABLE 1-A-continued

| No. | Starting material | product | Yield (%) |
|---|---|---|---|
| 17 | | | 23 |
| 18 | | | 20 |
| 19 | | | 22 |

TABLE 1-A-continued

| No. | Starting material | product | Yield (%) |
|---|---|---|---|
| 20 | | | 17 |
| 21 | | | 21 |

TABLE 1-A-continued

| No. | Starting material | product | Yield (%) |
|---|---|---|---|
| 22 | (structure with naphthyl, phenyl, thiophene, anhydride, adamantyl, BrCH₂CH₂CH(CH₃)₂) | (structure with R₂ = —CH₂CH₂CH(CH₃)₂) | 22 |
| 23 | (structure with CH₃, thiophene-Br, anhydride, CH₂CCH₃, and Br—(CH₂)₄—C₆H₄—CN) | (structure with R₂ = —(CH₂)₄—C₆H₄—CN) | 19 |

TABLE 1-A-continued

| No. | Starting material | product | Yield (%) |
|---|---|---|---|
| 24 | (structure with CH₃, H, O, furan, adamantane, and BrCH₂(CH₂)₂ group with 3,5-dimethoxyphenyl) | (structure with CH₃, R₂, O, furan, adamantane; R₂ = CH₂(CH₂)₂ with 3,5-dimethoxyphenyl) | 18 |
| 25 | (structure with CH₃, H, S-phenyl, CCl₂, and BrCH₂CH₂ group with p-tolyl) | (structure with CH₃, R₂, S-phenyl, CCl₂; R₂ = —CH₂CH₂ with p-tolyl) | 21 |

TABLE 1-A-continued

| No. | Starting material | product | Yield (%) |
|---|---|---|---|
| 26 | (structure with NO2-phenyl, H, anhydride, adamantane, naphthalene) | (structure with NO2-phenyl, R2, anhydride, adamantane, naphthalene) | 24 |
| 27 | (bis(4-phenoxy)phenyl-CF2Br structure); (thiophene-Cl, CH3, H, anhydride, bicyclic structure); Br(CH2)4OC(CH2)3NO2, O | R2 = —CF2(C6H4-O-C6H4-CH2Cl); (thiophene-Cl, CH3, R2, anhydride, bicyclic); R2 = —(CH2)4OC(CH2)3NO2, O | 18 |
| 28 | (phenyl, H, anhydride, adamantane, thiophene-OCH3-phenyl structure); BrCH2CH2OH | (phenyl, R2, anhydride, adamantane, thiophene-OCH3-phenyl); R2 = —CH2CH2OH | 16 |

TABLE 1-A-continued

| No. | Starting material | product | Yield (%) |
|---|---|---|---|
| 29 | (structure with CH₃, H, adamantane, N-CH₃-phenyl, anhydride; Br—CH₂CH—CH₂—OC₄H₉ with CH₃) | (structure with CH₃, R₂, adamantane, N-CH₃-phenyl, anhydride; R₂ = —CH₂CHCH₂OC₄H₉ with CH₃) | 19 |
| 30 | (structure with C₃H₇, H, adamantane, dibenzofuran-type, 4-chlorophenoxyphenyl, anhydride; BrCH₂—) | (structure with C₃H₇, R₂, adamantane, dibenzofuran-type, 4-chlorophenoxyphenyl, anhydride; R₂ = —CH₂—) | 21 |

TABLE 1-A-continued
| No. | Starting material | product | Yield (%) |
|---|---|---|---|
| 31 | 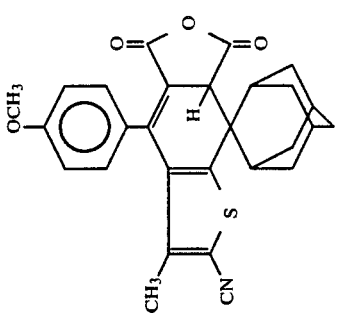<br>Br—CH$_2$CH$_2$CH$_2$—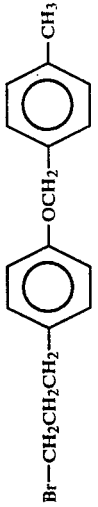 | 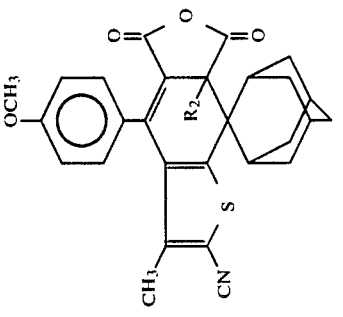<br>R$_2$ = —CH$_2$CH$_2$CH$_2$—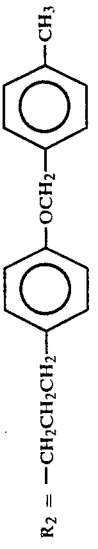 | 20 |
| 32 | <br>BrCH$_2$CCH$_3$<br>‖<br>O | <br>R$_2$ = —CH$_2$CCH$_3$<br>‖<br>O | 20 |

TABLE 1-A-continued

| No. | Starting material | product | Yield (%) |
|---|---|---|---|
| 33 | (structure) | (structure) | 19 |
| 34 | (structure) | (structure) | 21 |

TABLE 1-A-continued

| No. | Starting material | product | Yield (%) |
|---|---|---|---|
| 35 | (structure with C₂H₅-phenyl, anhydride, adamantane, S-OCH₃ thioether, Br(CH₂)₂OCCH₃) | (structure with R₂ = -(CH₂)₂OCCH₃, O) | 20 |
| 36 | (structure with CH₃, anhydride, adamantane, N-phenyl, Br(CH₂)₃, 4-cyanophenyl 4-hydroxybenzoate) | (structure with R₂ = -(CH₂)₃, 4-cyanophenyl benzoate) | 20 |

TABLE 1-A-continued

| No. | Starting material | product | Yield (%) |
|---|---|---|---|
| 37 | (structure with CH₃, H, S, adamantyl, anhydride; Br(CH₂)₃OC(O)—CH₂—Ph) | (structure with CH₃, R₂, S, adamantyl, anhydride; R₂ = —(CH₂)₃OC(O)—CH₂—Ph) | 21 |
| 38 | (structure with Ph, H, S, adamantyl, anhydride; BrCH₂COCH₂CF₃) | (structure with Ph, R₂, S, adamantyl, anhydride; R₂ = —CH₂COCH₂CF₃) | 20 |

TABLE 1-A-continued

| No. | Starting material | product | Yield (%) |
|---|---|---|---|
| 39 | | | 22 |
| 40 | | | 19 |
| 41 | | | 20 |

TABLE 1-A-continued

| No. | Starting material | product | Yield (%) |
|---|---|---|---|
| 42 | [structure with anhydride, phenyl, O, CH₃ groups] + Br(CH₂)₃CN with dibenzyl amide | [structure] R₂ = (CH₂)₃CN | 18 |
| 43 | [structure with anhydride, phenyl, S, Br, Cl] + BrCH₂OCC₂H₅ (O) | [structure] R₂ = —CH₂OCOC₂H₅ | 21 |

TABLE 1-A-continued

| No. | Starting material | product | Yield (%) |
|---|---|---|---|
| 44 | (structure with NC₂H₅, CH₃, S, H, adamantyl); BrC₂H₅ | (structure with NC₂H₅, CH₃, S, R₂, adamantyl, CH₃); R₂ = —C₂H₅ | 19 |
| 45 | (structure with N-phenyl, C₄H₉, O, H, adamantyl); ClCH₂-phenyl | (structure with N-phenyl, C₄H₉, O, R₂, adamantyl); R₂ = —CH₂-phenyl | 20 |
| 46 | (structure with N-CH₂-phenyl, phenyl, N-phenyl, H, adamantyl); BrCH₂CF₃ | (structure with N-CH₂-phenyl, phenyl, N-phenyl, R₂, adamantyl); R₂ = —CH₂CF₃ | 18 |

TABLE 1-A-continued

| No. | Starting material | product | Yield (%) |
|---|---|---|---|
| 47 | (structure with CH₃CH(CH₃)CH₂, CH₃, H, S, Br, N—C₄H₉, and BrC₄H₉) | (structure with CH(CH₃)₂, CH₂, CH₃, R₂, S, Br, N—C₄H₉; R₂ = —C₄H₉) | 22 |
| 48 | (structure with phenyl groups, H, S, cyclohexenyl, N—(CH₂)₅—phenyl, and Br—(CH₂)₅—phenyl) | (structure with phenyl groups, R₂, S, cyclohexenyl, N—(CH₂)₅—phenyl; R₂ = —(CH₂)₅—phenyl) | 17 |
| 49 | (structure with CH₃, H, Cl, O, phenyl, N-(4-C₂H₅-phenyl), and cyclohexyl with CN and Br) | (structure with CH₃, R₂, Cl, O, phenyl, N-(4-C₂H₅-phenyl); R₂ = cyclohexyl-CN) | 23 |

TABLE 1-A-continued

| No. | Starting material | product | Yield (%) |
|---|---|---|---|
| 50 | [structure with CH₃, NCH₂CH₂OH, H, S, NO₂ substituents on fused ring system] I—CH₃ | [corresponding product structure] R₂ = —CH₃ | 19 |
| 51 | [structure with CH₃, NCH₂CH₂OCH₃, H, S, phenyl substituents] Br—CH₂CH₂OCH₃ | [corresponding product structure] R₂ = —CH₂CH₂OCH₃ | 21 |
| 52 | [structure with N-CH₂-(4-tolyloxyphenyl), CH₃, H, Br, O, CH₃ substituents] Cl—CH₂-(4-tolyloxyphenyl) | [corresponding product structure] R₂ = —CH₂-(4-tolyloxyphenyl) | 18 |

TABLE 1-A-continued

| No. | Starting material | product | Yield (%) |
|---|---|---|---|
| 53 | (structure with phenyl-CH$_2$, N-CH$_3$ aniline, adamantane spiro, imide N-CH$_2$CH$_2$CH$_2$CC$_2$H$_5$(=O), 1—CH$_3$) | (corresponding product, R$_2$ = —CH$_3$) | 20 |
| 54 | (structure with 4-Cl-phenyl, thiophene, adamantane spiro, imide N-(4-NO$_2$-phenyl), 1—CH$_3$) | (corresponding product, R$_2$ = —CH$_3$) | 19 |

TABLE 1-A-continued
| No. | Starting material | | product | Yield (%) |
|---|---|---|---|---|
| 55 | 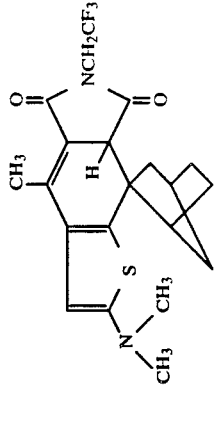 I—CH₃ | | 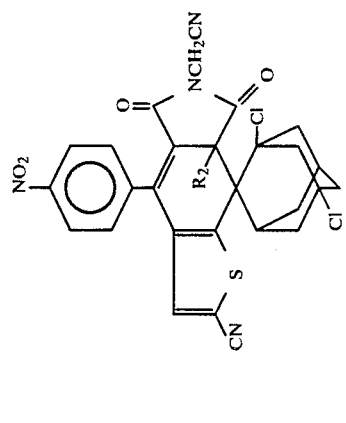 R₂ = —CH₃ | 19 |
| 56 | 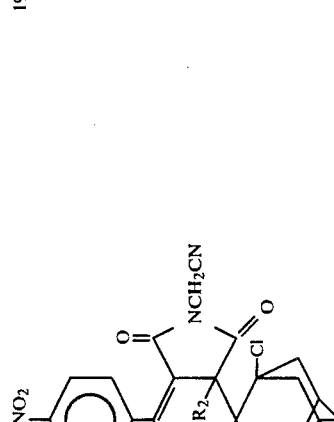 Br—C₂H₅ | | 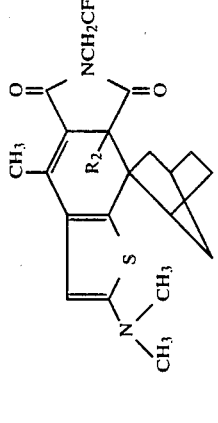 R₂ = —C₂H₅ | 21 |
| 57 | 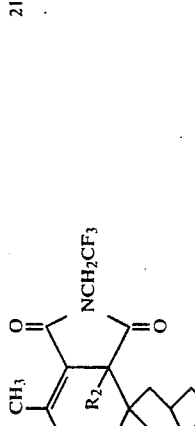 Br—C₂H₅ | | 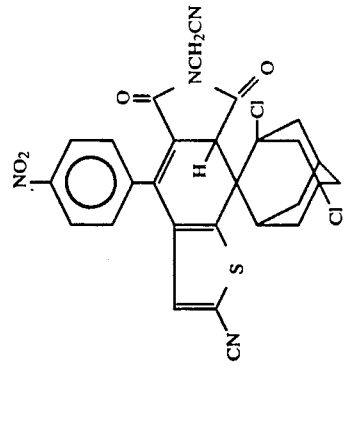 R₂ = —C₂H₅ | 19 |

TABLE 1-A-continued

| No. | Starting material | product | Yield (%) |
|---|---|---|---|
| 58 | (structure with N-CH₂CH₂CN, N(CH₃)₂, CH₃, S, OC₂H₅, CH₃, H; Br—C₂H₅) | (structure with NCH₂CH₂CN, N(CH₃)₂, CH₃, S, CH₃, R₂; R₂ = —C₂H₅) | 20 |
| 59 | (structure with NCH₂OCOC₄H₉, CH₃, OC₂H₅, S, CH₃, H; Br—C₂H₅) | (structure with NCH₂OCOC₄H₉, CH₃, OC₂H₅, S, CH₃, R₂; R₂ = —C₂H₅) | 20 |

TABLE 1-B

| | Elemental analysis (%) | | | | | | | | | | | |
|---|---|---|---|---|---|---|---|---|---|---|---|---|
| | Calculated | | | | | | Found | | | | | |
| No. | C | H | N | O | S | Others | | C | H | N | O | S | Others |
| 4 | 78.65 | 6.37 | — | 8.99 | 5.99 | — | | 78.42 | 6.47 | — | 9.01 | 6.10 | — |
| 5 | 60.12 | 4.47 | — | 8.59 | 5.73 | Br 14.30 F 6.80 | | 60.21 | 4.52 | — | 8.63 | 5.65 | Br 14.24 F 6.79 |
| 6 | 70.83 | 7.29 | 2.43 | 13.89 | 5.56 | — | | 70.72 | 7.33 | 2.46 | 13.82 | 5.67 | — |
| 7 | 72.20 | 6.75 | — | 8.75 | 5.83 | Cl 6.46 | | 72.29 | 6.71 | — | 8.81 | 5.72 | Cl 6.47 |
| 8 | 79.32 | 7.12 | — | 13.56 | — | — | | 79.38 | 7.09 | — | 13.52 | — | — |
| 9 | 71.97 | 6.16 | — | 10.37 | — | Cl 11.49 | | 71.89 | 6.24 | — | 10.42 | — | Cl 11.45 |
| 10 | 70.46 | 6.42 | 2.57 | 14.68 | 5.87 | — | | 70.41 | 6.49 | 2.62 | 14.73 | 5.75 | — |
| 11 | 58.69 | 3.54 | — | 10.79 | 5.40 | Cl 11.96 F 9.61 | | 58.60 | 3.58 | — | 10.72 | 5.43 | Cl 11.94 F 9.73 |
| 12 | 75.45 | 5.99 | 4.19 | 14.37 | — | — | | 75.41 | 5.92 | 4.24 | 14.43 | — | — |
| 13 | 62.31 | 5.19 | 2.14 | 7.33 | — | Cl 10.83 Br 12.20 | | 62.37 | 5.14 | 2.09 | 7.37 | — | Cl 10.80 Br 12.23 |
| 14 | 67.50 | 6.52 | — | 18.00 | — | Cl 7.98 | | 67.51 | 6.46 | — | 17.93 | — | Cl 8.10 |
| 15 | 76.43 | 6.37 | 2.97 | 10.19 | — | F 4.03 | | 76.49 | 6.32 | 2.93 | 10.24 | — | F 4.02 |
| 16 | 69.57 | 5.41 | 2.71 | 9.28 | 6.18 | Cl 6.85 | | 69.64 | 5.43 | 2.66 | 9.24 | 6.17 | Cl 6.86 |
| 17 | 59.73 | 4.98 | 6.33 | 21.72 | 7.24 | — | | 59.67 | 4.93 | 6.40 | 21.64 | 7.36 | — |
| 18 | 64.88 | 5.24 | 7.10 | 10.81 | — | Cl 11.98 | | 64.79 | 5.29 | 7.04 | 10.83 | — | Cl 12.05 |
| 19 | 72.58 | 7.26 | 2.82 | 9.68 | — | F 7.66 | | 72.54 | 7.24 | 2.78 | 9.74 | — | F 7.70 |
| 20 | 75.98 | 6.15 | — | 11.92 | 5.96 | — | | 75.92 | 6.18 | — | 11.94 | 5.95 | — |
| 21 | 60.92 | 4.76 | 2.22 | 10.15 | 5.08 | Cl 16.87 | | 60.90 | 4.78 | 2.19 | 10.17 | 5.11 | Cl 16.85 |
| 22 | 79.72 | 6.29 | — | 8.39 | 5.59 | — | | 79.68 | 6.31 | — | 8.36 | 5.64 | — |
| 23 | 62.85 | 5.07 | 2.37 | 10.81 | 5.41 | Br 13.50 | | 62.83 | 5.09 | 2.34 | 10.84 | 5.41 | Br 13.50 |
| 24 | 71.68 | 6.17 | — | 18.50 | — | F 3.66 | | 71.64 | 6.14 | — | 18.56 | — | F 3.67 |
| 25 | 67.40 | 5.25 | — | 8.70 | 5.80 | Cl 12.85 | | 64.36 | 5.29 | — | 8.74 | 5.76 | Cl 12.85 |
| 26 | 69.55 | 4.52 | 1.98 | 13.57 | — | Cl 5.01 F 5.37 | | 69.52 | 4.56 | 1.96 | 13.52 | — | Cl 5.05 F 5.39 |
| 27 | 57.53 | 5.37 | 2.68 | 21.48 | 6.14 | Cl 6.80 | | 57.50 | 5.34 | 2.72 | 21.47 | 6.17 | Cl 6.80 |
| 28 | 73.00 | 5.70 | — | 15.21 | 6.08 | — | | 72.96 | 5.72 | — | 15.24 | 6.07 | — |
| 29 | 76.86 | 7.96 | 2.72 | 12.43 | — | — | | 76.82 | 7.97 | 2.76 | 12.42 | — | — |
| 30 | 75.67 | 5.66 | — | 12.94 | — | Cl 5.73 | | 75.62 | 5.69 | — | 12.97 | — | Cl 5.74 |
| 31 | 75.52 | 6.85 | 1.96 | 11.19 | 4.48 | — | | 75.47 | 6.86 | 1.99 | 11.17 | 4.51 | — |
| 32 | 72.80 | 7.11 | — | 13.39 | 6.69 | — | | 72.84 | 7.12 | — | 13.35 | 6.68 | — |
| 33 | 73.72 | 6.14 | — | 13.65 | — | F 6.48 | | 73.69 | 6.12 | — | 13.69 | — | F 6.49 |
| 34 | 78.42 | 6.99 | — | 14.59 | — | — | | 78.39 | 7.01 | — | 14.60 | — | — |
| 35 | 72.45 | 6.42 | — | 15.09 | 6.04 | — | | 72.41 | 6.46 | — | 15.07 | 6.06 | — |
| 36 | 77.95 | 5.74 | 4.23 | 12.08 | — | — | | 77.92 | 5.76 | 4.24 | 12.08 | — | — |
| 37 | 72.79 | 6.62 | — | 14.71 | 5.88 | — | | 72.73 | 6.60 | — | 14.76 | 5.91 | — |
| 38 | 64.21 | 4.61 | — | 14.76 | 5.90 | F 10.52 | | 64.18 | 4.64 | — | 14.74 | 5.93 | F 10.51 |
| 39 | 73.12 | 6.81 | — | 14.34 | 5.73 | — | | 73.09 | 6.78 | — | 14.38 | 5.75 | — |
| 40 | 69.29 | 6.04 | 3.67 | 21.00 | — | — | | 69.32 | 6.07 | 3.62 | 20.99 | — | — |
| 41 | 67.94 | 4.72 | 2.20 | 12.58 | — | Br 12.56 | | 67.87 | 4.69 | 2.28 | 12.61 | — | Br 12.55 |
| 42 | 79.02 | 6.58 | 2.14 | 12.60 | — | — | | 79.07 | 6.54 | 2.17 | 12.56 | — | — |
| 43 | 54.79 | 4.06 | — | 16.23 | 5.41 | Cl 5.99 Br 13.51 | | 54.83 | 4.09 | — | 16.17 | 5.42 | Cl 5.96 Br 13.52 |
| 44 | 73.35 | 7.58 | 3.42 | 7.82 | 7.82 | — | | 73.27 | 7.59 | 3.46 | 7.86 | 7.81 | — |
| 45 | 81.36 | 6.97 | 2.64 | 9.04 | — | — | | 81.33 | 6.99 | 2.66 | 9.05 | — | — |
| 46 | 75.95 | 5.54 | 4.43 | 5.06 | — | F 9.02 | | 75.92 | 5.50 | 4.46 | 5.07 | — | F 9.05 |
| 47 | 63.75 | 7.33 | 2.56 | 5.86 | 5.86 | Br 14.64 | | 63.72 | 7.30 | 2.59 | 5.88 | 5.89 | Br 14.62 |
| 48 | 81.62 | 7.09 | 2.03 | 4.63 | 4.63 | — | | 81.60 | 7.07 | 2.06 | 4.61 | 4.66 | — |
| 49 | 74.94 | 5.72 | 4.86 | 8.33 | — | Cl 6.15 | | 74.91 | 5.73 | 4.88 | 8.30 | — | Cl 6.18 |
| 50 | 62.44 | 5.88 | 6.33 | 18.10 | 7.24 | — | | 62.47 | 5.86 | 6.31 | 18.07 | 7.28 | — |
| 51 | 71.29 | 6.93 | 2.77 | 12.67 | 6.34 | — | | 71.29 | 6.96 | 2.73 | 12.61 | 6.41 | — |
| 52 | 72.37 | 5.78 | 1.76 | 10.05 | — | Br 10.04 | | 72.33 | 5.81 | 1.77 | 10.01 | — | Br 10.08 |
| 53 | 79.43 | 6.98 | 5.01 | 8.59 | — | — | | 79.40 | 6.99 | 5.03 | 8.59 | — | — |
| 54 | 67.32 | 4.73 | 4.91 | 11.22 | 5.61 | Cl 6.21 | | 67.36 | 4.70 | 4.90 | 11.17 | 5.64 | Cl 6.23 |
| 55 | 58.69 | 3.71 | 9.45 | 10.79 | 5.40 | Cl 11.96 | | 58.66 | 3.70 | 9.47 | 10.83 | 5.36 | Cl 11.98 |
| 56 | 61.06 | 5.97 | 6.19 | 7.08 | 7.08 | F 12.61 | | 61.02 | 5.99 | 6.21 | 7.06 | 7.09 | F 12.62 |
| 57 | 76.51 | 5.54 | 1.94 | 11.09 | — | Cl 4.91 | | 76.58 | 5.48 | 1.91 | 11.12 | — | Cl 4.90 |
| 58 | 70.42 | 7.51 | 3.29 | 11.27 | 7.51 | — | | 70.38 | 7.49 | 3.32 | 11.26 | 7.55 | — |
| 59 | 66.42 | 7.38 | 2.58 | 17.71 | 5.90 | — | | 66.44 | 7.36 | 2.56 | 17.73 | 5.90 | — |

EXAMPLES 60–118

In each run, 0.5 part by weight of each of the compounds (1) to (59) produced in Examples 1 to 59 and 10 parts by weight of poly(methyl methacrylate) were dispersed in 100 parts by weight of benzene, and the dispersion was cast onto a slide glass (11.2×3.7 cm) to form a film having a thickness of 0.1 mm. The durability of this photochromic film in the repetition of color formation and extinction (repetitive durability) was measured under the conditions described below.

Excitation light source: Xenon lamp (250 W); Irradiation time 3 seconds
Color extinction light source: Xeon lamp (250 W; light of a wavelength 400 nm and below was cut off by providing a filter); Irradiation time 30 seconds.

The repetitive durability was defined as the number of repetitions of color formation-extinction which was required for the initial color density of the film to decrease to half.

Furthermore, light from the above excitation light source was irradiated on the above film, and the color density of the film measured at this time was made an initial density. The film was put in an oven at 80° C., and the thermal stability of the formed color of the film was evaluated. The thermal stability was defined as the time required for the above initial density value to decrease to half.

The results are shown in Table 2.

For Comparison, films were prepared as above using compounds (60) and (61) below, and their durability and thermal stability were measured.

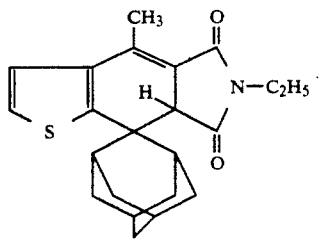
(60)

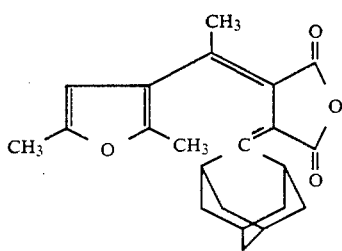
(61)

TABLE 2

| Example No. | Photochromic compound No. | Number of repetitions | Thermal stability (hours) |
|---|---|---|---|
| 60 | 1 | 3000 | 1200 |
| 61 | 2 | 2800 | 900 |
| 62 | 3 | 3500 | 1000 |
| 63 | 4 | 3300 | 1210 |
| 64 | 5 | 3100 | 1250 |
| 65 | 6 | 2900 | 1200 |
| 66 | 7 | 2950 | 1230 |
| 67 | 8 | 3230 | 1190 |
| 68 | 9 | 3110 | 1180 |
| 69 | 10 | 3380 | 1210 |
| 70 | 11 | 3210 | 1190 |
| 71 | 12 | 3300 | 1150 |
| 72 | 13 | 2900 | 880 |
| 73 | 14 | 2950 | 920 |
| 74 | 15 | 2850 | 900 |
| 75 | 16 | 3150 | 850 |
| 76 | 17 | 3050 | 800 |
| 77 | 18 | 3000 | 900 |
| 78 | 19 | 3250 | 900 |
| 79 | 20 | 2950 | 1250 |
| 80 | 21 | 3110 | 1200 |
| 81 | 22 | 3120 | 1200 |
| 82 | 23 | 3400 | 820 |
| 83 | 24 | 3380 | 1190 |
| 84 | 25 | 2780 | 830 |
| 85 | 26 | 3130 | 1200 |
| 86 | 27 | 3190 | 900 |
| 87 | 28 | 3090 | 1220 |
| 88 | 29 | 3120 | 1250 |
| 89 | 30 | 2850 | 1200 |
| 90 | 31 | 2960 | 1210 |
| 91 | 32 | 3010 | 1190 |
| 92 | 33 | 3020 | 1250 |
| 93 | 34 | 3030 | 1200 |
| 94 | 35 | 3010 | 1200 |
| 95 | 36 | 2880 | 1180 |
| 96 | 37 | 2980 | 1190 |
| 97 | 38 | 3110 | 1210 |
| 98 | 39 | 3120 | 1200 |
| 99 | 40 | 3220 | 1250 |
| 100 | 41 | 2980 | 1200 |
| 101 | 42 | 3100 | 880 |
| 102 | 43 | 3000 | 880 |
| 103 | 44 | 3240 | 1130 |
| 104 | 45 | 2930 | 1190 |
| 105 | 46 | 2810 | 1100 |
| 106 | 47 | 2790 | 820 |
| 107 | 48 | 2860 | 1150 |
| 108 | 49 | 3080 | 840 |
| 109 | 50 | 3060 | 1090 |
| 110 | 51 | 3030 | 1130 |
| 111 | 52 | 3010 | 880 |
| 112 | 53 | 3120 | 1100 |
| 113 | 54 | 2880 | 1100 |
| 114 | 55 | 2970 | 1150 |
| 115 | 56 | 2780 | 850 |
| 116 | 57 | 3100 | 1120 |
| 117 | 58 | 3000 | 860 |
| 118 | 59 | 3360 | 1100 |
| Comparison 1 | (60) | 500 | 2 (sec.) |
| Comparison 2 | (61) | 300 | 250 |

We claim:

1. A compound represented by the following formula [I]

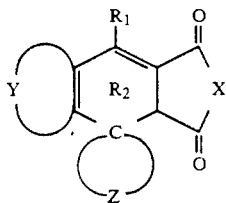

[I]

wherein

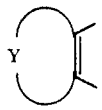

represents a divalent benzene ring, a divalent naphthalene ring, a divalent 5-membered monoheterocyclic group having one hetero atom, or a fused heterocyclic group resulting from fusion of a benzene ring to said monoheterocyclic group, each of which may be substituted by at least one atom or group selected from the group consisting of halogen atoms, nitro groups, cyano groups, $C_1$-$C_4$ alkyl groups, $C_1$-$C_4$ alkoxy groups, $C_1$-$C_4$ alkylamino groups, di($C_1$-$C_4$)alkylamino groups, phenyl groups and $C_1$-$C_4$ alkoxyphenyl groups, and when two alkyl groups are substituted on each said ring, they may be bonded to each other to form a ring, $R_1$ represents a $C_1$-$C_6$ alkyl group which may be substituted by a halogen atom or a $C_1$-$C_4$ alkoxy group; a $C_7$-$C_{10}$ aralkyl group may be substituted by a halogen atom; a $C_6$-$C_{10}$ aryl group which may be substituted by a halogen atom, a nitro group or a $C_1$-$C_4$ alkoxy group;

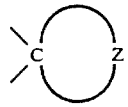

represents a norbornylidene or adamantylidene group which may be substituted by at least one atom or group selected from the group consisting of hydroxyl groups, nitro groups, cyano groups, carboxyl groups, halogen atoms, $C_1$-$C_4$ alkylamino groups, di($C_1$-$C_4$) alkylamino groups, $C_1$-$C_4$ alkyl groups, $C_1$-$C_4$ alkoxy groups, $C_1$-$C_2$ haloalkyl groups, $C_2$-$C_{10}$ alkoxycarbonyl groups, ($C_1$-$C_4$)alkylcarbonyl($C_1$-$C_4$)alkyl groups, $C_7$-$C_{15}$ aralkyl groups, $C_7$-$C_{15}$ aralkoxy groups, $C_6$-$C_{10}$ aryl groups and $C_6$-$C_{10}$ aryloxy groups, X represents an oxygen atom or the group >N—$R_3$ wherein $R_3$ represents a $C_1$-$C_6$ alkyl group, a $C_5$-$C_7$ cycloalkyl group, a $C_7$-$C_{10}$ aralkyl group or a $C_6$-$C_{10}$ aryl group, each of which may be substituted by at least one atom or group selected from the group consisting of halogen atoms, cyano groups, nitro groups, hydroxyl groups, $C_1$-$C_5$ alkoxy groups, $C_6$-$C_{10}$ aryloxy groups,

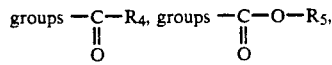

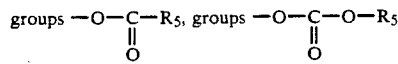

and

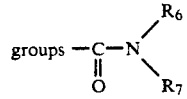

wherein $R_4$ represents a $C_1$-$C_4$ alkyl group or a $C_6$-$C_{10}$ aryl group each of which may be substituted by a halogen atom, $R_5$ represents a $C_1$-$C_4$ alkyl group which may be substituted by a halogen atom or a nitro group, or a $C_6$-$C_{10}$ aryl group or a $C_7$-$C_{10}$ aralkyl group each of which may be substituted by a cyano group, and $R_6$ and $R_7$ are identical or different and each represents a hydrogen atom, a $C_1$-$C_4$ alkyl group, a $C_7$-$C_{10}$ aralkyl group or a $C_6$-$C_{10}$ aryl group, and $R_2$ represents a $C_1$-$C_6$ alkyl group, a $C_5$-$C_7$ cycloalkyl group, a ($C_5$-$C_7$)cycloalkyl($C_1$-$C_4$)alkyl group or a $C_7$-$C_{10}$ aralkyl group, each of which may be substituted by at least one atom or group selected from the group consisting of halogen atoms, cyano groups, nitro groups, hydroxyl groups, $C_1$-$C_6$ alkoxy groups, $C_6$-$C_{10}$ aryloxy groups optionally substituted by a halogen atom, $C_7$-$C_{15}$ aralkoxy groups,

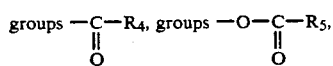

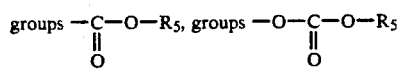

and

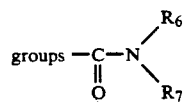

wherein $R_4$ represents a $C_1$-$C_4$ alkyl group which may be substituted by a halogen atom, $R_5$ represents a $C_1$-$C_4$ alkyl group which may be substituted by a cyano group, and $R_6$ and $R_7$ are identical or different and each represents a hydrogen atom, a $C_1$-$C_4$ alkyl group, a $C_7$-$C_{10}$ aralkyl group or a $C_6$-$C_{10}$ aryl group.

2. The compound of claim 1 in which X in formula [I] is an oxygen atom.

3. The compound of claim 1 in which X in formula [I] is the group >N—$R_3$ wherein $R_3$ represents a $C_1$-$C_6$ alkyl group, a $C_5$-$C_7$ cycloalkyl group, a $C_7$-$C_{10}$ aralkyl group or a $C_6$-$C_{10}$ aryl group, each of which may be substituted by at least one atom or group selected from the class consisting of halogen atoms, cyano groups, nitro groups, hydroxyl groups, $C_1$-$C_5$ alkoxy groups, $C_6$-$C_{10}$ aryloxy groups,

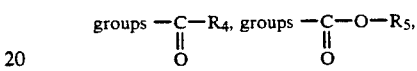

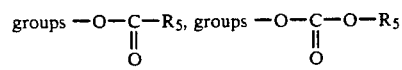

and

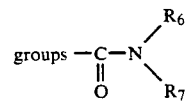

wherein $R_4$ represents a $C_1$-$C_4$ alkyl group or a $C_6$-$C_{10}$ aryl group each of which may be substituted by a halogen atom, $R_5$ represents a $C_1$-$C_4$ alkyl group which may be substituted by a halogen atom or a nitro group, or a $C_6$-$C_{10}$ aryl group or a $C_7$-$C_{10}$ aralkyl group each of which may be substituted by a cyano group, and $R_6$ and $R_7$ are identical or different and each represents a hydrogen atom, a $C_1$-$C_4$ alkyl group, a $C_7$-$C_{10}$ aralkyl group or a $C_6$-$C_{10}$ aryl group.

4. The compound of claim 1 in which X in formula [I] is the group >N—$R_3$ in which $R_3$ represents a $C_1$-$C_6$ alkyl group, a $C_5$-$C_7$ cycloalkyl group or a $C_7$-$C_{10}$ aralkyl group, each of which may be substituted by a halogen atom, a cyano group, a nitro group, a $C_1$-$C_6$ alkoxy group or the

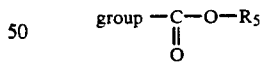

wherein $R_5$ represents a $C_1$-$C_4$ alkyl group which may be substituted by a halogen atom or a nitro group, or a $C_6$-$C_{10}$ aryl group which may be substituted by a cyano group.

5. The compound of claim 1 in which

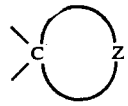

in formula [I] represents an adamantylidene group which may have a substituent.

6. The compound of claim 1 in which in formula [I],

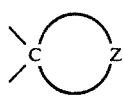

represents an adamantylidene group which may have a substituent, and X is an oxygen atom.

7. The compound of claim 1 in which

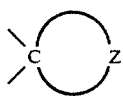

in formula [I] represents an adamantylidene or norbornylidene group substituted by at least one atom or group selected from the class consisting of halogen atoms, $C_1$–$C_4$ alkyl groups, $C_1$–$C_4$ alkoxy groups, $C_1$–$C_4$ alkylamino groups, di($C_1$–$C_4$)alkylamino groups and ($C_1$–$C_4$)alkylcarbonyl($C_1$–$C_4$)alkyl groups.

8. The compound of claim 1 in which $R_1$ in formula [I] represents a $C_1$–$C_6$ alkyl group; a $C_7$–$C_{10}$ aralkyl group; or a $C_6$–$C_{10}$ aryl group which may be substituted by a halogen atom, a nitro group or a $C_1$–$C_4$ alkoxy group.

9. The compound of claim 1 in which

in formula [I] represents a divalent benzene ring, a divalent naphthalene ring, a divalent furan ring, a divalent pyrrole ring, a divalent thiophene ring, a divalent benzofuran ring, a divalent indole ring, a divalent benzothiophene ring or a divalent tetrahydrobenzothiophene group, each of which may be substituted by an atom or group selected from the class consisting of halogen atoms, nitro groups, cyano groups, $C_1$–$C_4$ alkyl groups, $C_1$–$C_4$ alkoxy groups, $C_1$–$C_4$ alkylamino groups, di($C_1$–$C_4$)alkylamino groups, phenyl groups and $C_1$–$C_4$ alkoxyphenyl groups.

10. The compound of claim 1 in which X represents an oxygen atom or the group >N—$R_3$ wherein $R_3$ represents a $C_1$–$C_6$ alkyl group which may be substituted by a halogen atom, a cyano group, or a $C_2$–$C_5$ alkoxycarbonyl group;

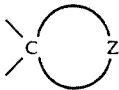

represents a norbornylidene or adamantylidene group; $R_1$ represents a $C_1$–$C_4$ alkyl group or a $C_6$–$C_{10}$ aryl group; $R_2$ is a $C_1$–$C_4$ alkyl group which may be substituted by a $C_2$–$C_5$ alkoxycarbonyl group; and

is a divalent furan ring, a divalent pyrrole ring or a divalent thiophene ring.

11. A process for producing the compound of formula [I] according to claim 1, which comprises reacting a compound represented by the following formula [II]

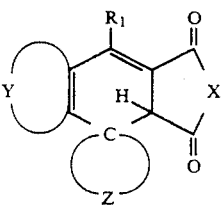

wherein

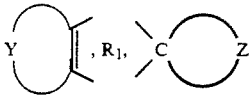

and X are as defined in general formula [I], with a halogen compound represented by the following general formula [III]

Hal—$R_2$ [III]

wherein Hal represents a chloride, bromine or iodine atom, and $R_2$ is as defined in formula [I] in claim 1, in the presence of an alkali metal or an alkali metal carbonate or after the compound of formula [I] is reacted with the alkali metal or its carbonate.

12. A photochromic composition comprising the compound of formula [I] according to claim 1 and a polymer.

13. The composition of claim 12 wherein the amount of the compound of formula [I] is 0.001 to 70 parts by weight per 100 parts by weight of the polymer.

14. A photomemory material composed of the composition of claim 12.

* * * * *